United States Patent
Jolly et al.

(10) Patent No.: US 8,126,572 B2
(45) Date of Patent: Feb. 28, 2012

(54) COCHLEAR IMPLANT ELECTRODE WITH ADJUSTABLE SUBDIVISION FOR MIDDLE EAR FUNCTIONS

(75) Inventors: Claude Jolly, Innsbruck (AT); S. Bryde Nielsen, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1304 days.

(21) Appl. No.: 11/082,238

(22) Filed: Mar. 15, 2005

(65) Prior Publication Data

US 2005/0216073 A1    Sep. 29, 2005

Related U.S. Application Data

(60) Provisional application No. 60/553,297, filed on Mar. 15, 2004.

(51) Int. Cl.
*A61N 1/05*    (2006.01)
*A61N 1/18*    (2006.01)

(52) U.S. Cl. .............. 607/137; 607/55; 607/56; 607/57; 600/379; 600/393

(58) Field of Classification Search ............. 607/55, 607/56, 57, 116, 125, 137, 3, 120; 600/373, 600/379, 393

See application file for complete search history.

(56) References Cited

U.S. PATENT DOCUMENTS

| 4,944,301 | A | * | 7/1990 | Widin et al. ............... 607/57 |
| 5,999,859 | A | * | 12/1999 | Jolly ...................... 607/137 |
| 6,205,360 | B1 | * | 3/2001 | Carter et al. .............. 607/57 |
| 6,208,882 | B1 | | 3/2001 | Lenarz et al. |
| 6,216,040 | B1 | * | 4/2001 | Harrison .................. 607/57 |
| 6,295,467 | B1 | | 9/2001 | Kollmeier et al. ......... 600/547 |
| 6,415,185 | B1 | | 7/2002 | Maltan ................... 607/57 |
| 6,456,866 | B1 | * | 9/2002 | Tyler et al. .............. 600/377 |
| 6,473,651 | B1 | * | 10/2002 | Kuzma et al. ............ 607/57 |
| 6,496,734 | B1 | | 12/2002 | Money ................... 607/56 |
| 6,636,768 | B1 | | 10/2003 | Harrison |
| 7,206,639 | B2 | * | 4/2007 | Jacobsen et al. ........... 607/57 |
| 2001/0056291 | A1 | | 12/2001 | Zilberman et al. |
| 2004/0078057 | A1 | * | 4/2004 | Gibson ................... 607/3 |

FOREIGN PATENT DOCUMENTS

WO    2004014270 A1    2/2004

OTHER PUBLICATIONS

International Search Report dated Aug. 31, 2006.

* cited by examiner

*Primary Examiner* — Carl H Layno
*Assistant Examiner* — Natasha Patel
(74) *Attorney, Agent, or Firm* — Sunstein Kann Murphy & Timbers LLP

(57) ABSTRACT

An electrode for use with a cochlear implant capable of being implanted in a subject is provided. The electrode includes a main electrode branch which provides functions to an inner ear of the subject and an adjustable subdivision connected to the main electrode for providing functions to a middle ear of the subject.

20 Claims, 5 Drawing Sheets

Subdivision rejoined to the main branch

COCHLEAR IMPLANT ELECTRODE WITH ADJUSTABLE SUBDIVISION FOR MIDDLE EAR FUNCTIONS

The present application claims priority from U.S. Provisional Application No. 60/553,297 which hereby incorporated herein, in its entirety, by reference.

TECHNICAL FIELD

The present invention relates to cochlear implants and, more particularly, to a cochlear implant electrode having an adjustable subdivision for attending to middle ear functions.

BACKGROUND ART

Cochlear implants are devices that include an implantable stimulator containing electronic circuitry, a coil for power and information transfer, and an electrode (and perhaps a counter electrode) usually placed under the temporalis muscle. The electrode may consist of single, double, or even triple branches. Each branch typically originates at the stimulator and is directed toward single or multiple cochleostomies through a mastoidectomy and a posterior tympanatomy, or through an alternate surgical approach such as a suprameatal approach. The single or multiple electrode branches are designed to go into the inner ear of the patient and stimulate neural tissue.

There are, in addition to such inner ear applications, concomitant applications to direct neural stimulation that would be beneficial to the patient. Some of these concomitant applications take place in the middle ear. These applications necessitate the placement of a device in the middle ear cavity without disrupting the cochlear implant electrodes that have been inserted into the inner ear.

SUMMARY OF THE INVENTION

In a first embodiment of the invention there is provided an electrode for use with a cochlear implant. The electrode is capable of being implanted in a subject and includes a main electrode branch that provides functions to an inner ear of the subject. The electrode also includes an adjustable subdivision, which is connected to the main electrode, for providing functions to a middle ear of the subject. In accordance with a related embodiment, the adjustable subdivision may be positioned within the middle ear with a rod like manipulator that is attached to the subdivision. In accordance with a further related embodiment, the rod like manipulator may be movable though a shaft located on the main electrode branch. In accordance with other related embodiments, the rod like manipulator may be disconnected from the subdivision and/or the subdivision may be affixed to any part of the main electrode branch.

In accordance with additional embodiments, the adjustable subdivision may include a transducer and/or the subdivision may provide a recording electrode to record signals from the middle ear. The adjustable subdivision may also provide a measuring electrode to sense a bio potential in the middle ear and/or the adjustable subdivision may provide a ground current electrode in the middle ear. In accordance with further embodiments, the adjustable subdivision may provide a reference electrode in the middle ear and/or the adjustable subdivision may provide an implantable hearing aid in the middle ear. In accordance with yet further embodiments, the adjustable subdivision may provide an implantable microphone in the middle ear and/or the adjustable subdivision may provide a biocompatible transducer in the middle ear. In accordance with another related embodiment, the adjustable subdivision may provide a drug delivery device in the middle ear.

In accordance with another embodiment of the invention, a recording electrode for use with a cochlear implant capable of being implanted in a subject is provided. The recording electrode includes a first section having a front end and is configured such that it may be disposed about a stapedius muscle of the subject's middle ear. The recording electrode also includes a second section having a back end. The back end includes a flexible extension for positioning the first section around the stapedius muscle. In accordance with a related embodiment, the front end of the recording electrode may include jaws that open to allow positioning of the first section about the stapedius muscle and/or the flexible extension may close the jaws about the stapedius muscle. In accordance with a further related embodiment, the recording electrode may include a rod for positioning the first section about the stapedius muscle from outside a mastoidectomy. Similarly, in accordance with another related embodiment, the recording electrode may include a rod for positioning the first section about the stapedius muscle via an anterior to a cochleostomy site. In accordance with yet further related embodiments, the first section may include a transducer and/or the first section may be shaped as a cuff.

DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

The present invention provides a cochlear implant electrode with at least one additional extra-cochlear subdivision for placement of a device located toward the tip of the subdivision into the middle ear cavity at a desired or profitable location. The invention includes devices to be placed in the middle ear and a mechanism to do so.

Such devices may be configured to provide a measuring electrode to sense the myogenic signal generated by the stapedius muscle or tendon, a measuring electrode to sense a bio potential, a ground current electrode, a reference electrode, an implantable hearing aid, an implantable microphone, a biocompatible transducer, and/or a drug delivery device. However, devices manufactured in accordance with the invention are not limited to the applications mentioned above.

For example, in accordance with one embodiment, the invention provides a recording electrode to measure the myogenic signal generated by the stapedius muscle and to include a mechanism for placing the small recording electrode on the stapedius tendon or muscle. It would be of great interest to have an electrode located on the stapedius tendon or stapedius muscle to measure the myogenic potential generated by contraction of the muscle. Such potentials reflect the most comfortable level of electric stimulation. Measuring the most comfortable level response to electric stimulation could be especially important for fitting young children with cochlear implants. Young children (as well as some adults) may not be capable of verbally or otherwise expressing a tolerable level of electric stimulation. The recording of the electrically evoked stapedius reflex threshold ("ESRT") would allow the objective fitting of the implant with such people.

The difficulty in recording the ESRT begins with the placement of a recording electrode on the stapedius tendon, or stapedius muscle. The recording electrode should be small and adapted to the small size of the tendon and muscle. It is extremely difficult to bring a measuring electrode to the tendon with the usual surgical tools after the stimulating electrode has been inserted into the cochlea. The space is too tight and any movement to approach the tendon or muscle carries the danger of displacing the inserted stimulating electrode.

This invention provides a simple way to bring a small recording electrode into contact with the stapedius muscle and tendon once the electrode array has been inserted into the cochlea. In accordance with embodiments of this invention, it is possible to maneuver the recording electrode without disruption of the stimulating electrode.

Figure 1:
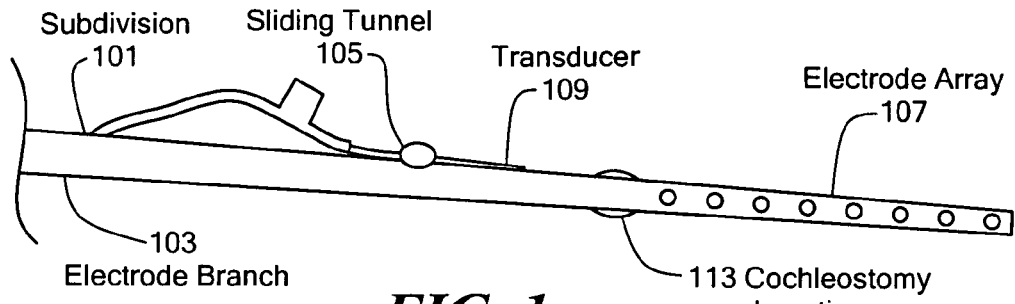
FIG. 1 is a graphical illustration of a partial view of an electrode with a subdivision for middle ear applications in accordance with one embodiment of the invention.
Figure 2:
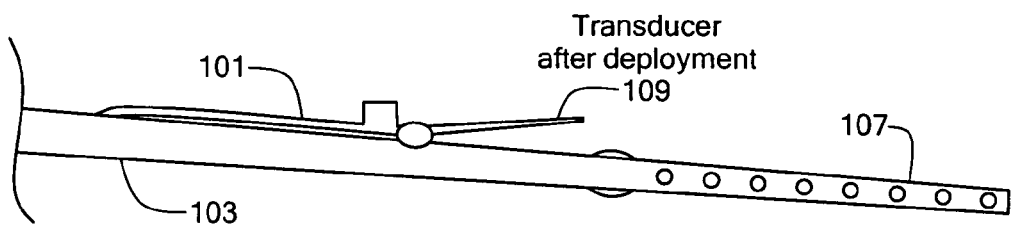
FIG. 2 is a graphical illustration of the electrode of FIG. 1 after deployment of the subdivision in the desired middle ear location.
Figure 3:
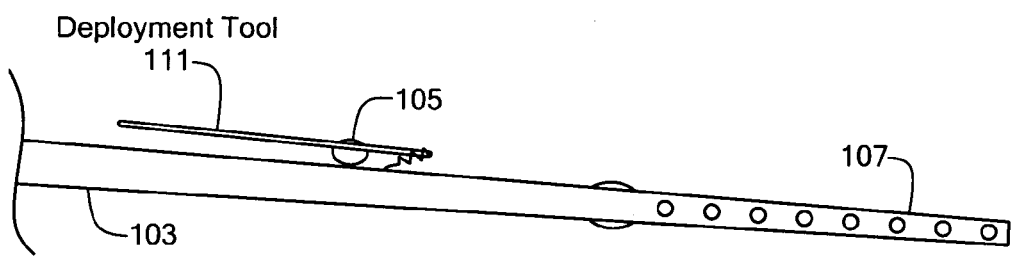
FIG. 3 is a graphical illustration showing one method of deploying the subdivision using a deployment tool.
Figure 4:
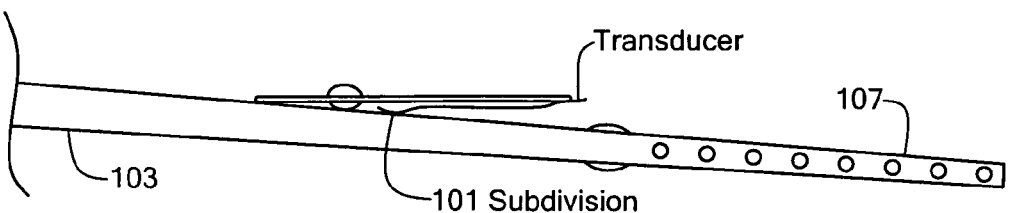
FIG. 4 is a graphical illustration of the electrode of FIG. 3 following deployment.

FIG. 1 is a graphical illustration of a partial view of an electrode with a subdivision for middle ear applications in accordance with one embodiment of the invention. A subdivision 101 off a main electrode branch 103 of a cochlear implant is tucked closely to the main electrode branch 103. Here, the subdivision is configured as a recording electrode which includes a transducer 109. The subdivision 101 is tucked in but movable through a shaft 105 built on the main electrode branch 103. By being tucked in, the subdivision 101 is unobtrusive while the stimulating inner ear electrode or electrode array 107 is inserted into the cochlea. Once the inner ear electrode 107 has been introduced fully into the cochlea, the tucked in subdivision part is moved closer to, and optionally in contact with, the exposed stapedius muscle or tendon as shown in FIG. 2. As shown in FIG. 3, tucked in subdivision (which includes a recording electrode in this embodiment) is attached to a long thin rod 111. The long thin rod 111 goes through the shaft 105 built on the main electrode branch 103 anterior to the cochleostomy site 113 and/or anterior to the facial recess. The long thin rod acts 111 as a deployment tool for bringing the recording electrode and/or its transducer 109 close to and, in contact with the tendon or muscle as shown in FIG. 4. The advantage of the long thin rod 111 is that it is small in size and is able to impart precise movement to the recording electrode for placement purposes.

Figure 5:
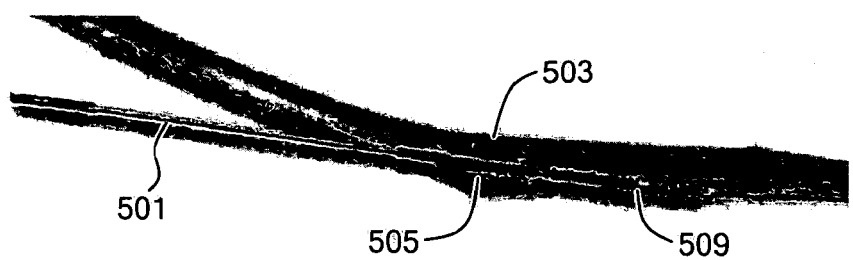
FIG. 5 is a photograph of an electrode in accordance with another embodiment of the invention.
Figure 6:
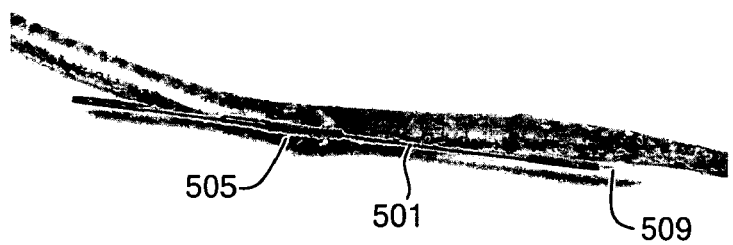
FIG. 6 is a photograph of the electrode of FIG. 5 following deployment in a desired location of the middle ear.

FIG. 5 is a photograph of an electrode in accordance with an embodiment of the invention. Here, a transducer 509 is attached to an arm 501 that can slide through a shaft 505 built on a main electrode branch 503. FIG. 6 is a photograph of the electrode of FIG. 5 following deployment or positioning in a desired location of the middle ear.

Figure 7:
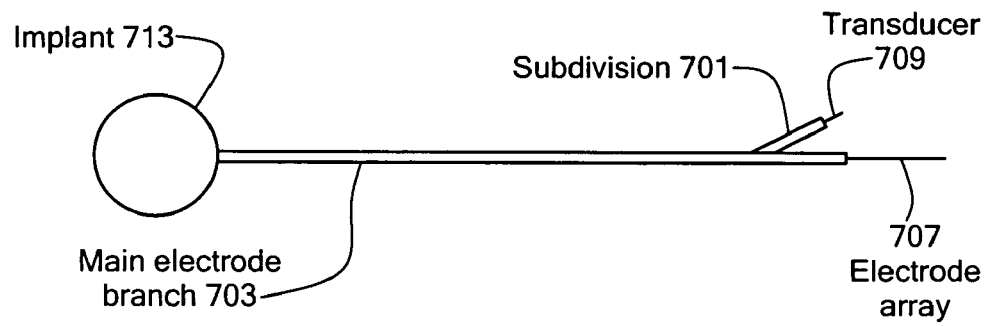
FIG. 7 is a graphical illustration of an electrode in accordance with another embodiment of the invention.

FIG. 7 is a graphical illustration of an electrode in accordance with another embodiment of the invention. In accordance with the embodiment of FIG. 7, a main electrode branch 703 of a cochlear implant 713 includes an electrode array 707. Connected to the main electrode branch 703 is a subdivision 701 located a distance from the implant 713. The subdivision 701 includes a transducer 709 similar to that described above.

An advantage of such an embodiment, is that it provides a configuration for a cochlear implant electrode that permits precise placement and fixation into the middle ear cavity of the secondary branch or subdivision 701 (terminated here with the transducer 709) without interference with the initially inserted inner ear electrode or electrode array 707. To this end, the subdivision 701 of the main electrode 703 provides at least one additional lead for the precise placement of a small device in the middle ear. Further, when the subdivision lead is connected to a thin rigid rod which may slide though a shaft, a device (such as the transducer 709 or a recording electrode) located at the tip of the subdivision lead can be precisely placed in the middle ear. During insertion via cochleostomy, the additional device may be in a retracted position such that it is tucked away at some distance from the cochleostomy so that it does not interfere with the insertion tools necessary to push the electrode into the cochlea. Further, after the main electrode branch 703 is inserted, the additional lead of the subdivision 701 can be slid down to the location where the device needs to be placed. The electrode lead of the subdivision 701 may carry most of the weight and mass of the additional device. In addition, for placement of a very small structure, such as a measuring electrode around the stapedius tendon, the connection of the subdivision 701 with the lead of the main electrode branch 703 though a tunnel decouples the tendon from the mass of the lead of the subdivision 701.

Figure 8:
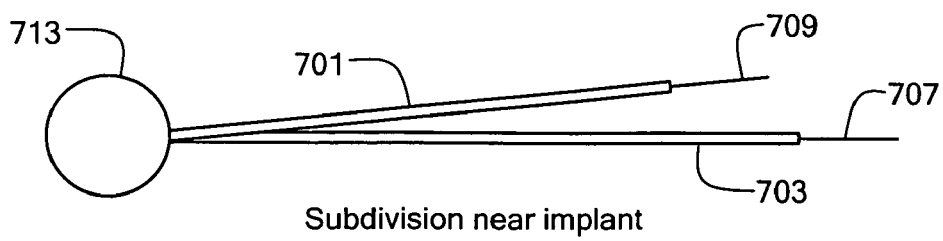
FIG. 8 is a graphical illustration of an electrode having a subdivision near an implant in accordance with a further embodiment of the invention.
Figure 9:
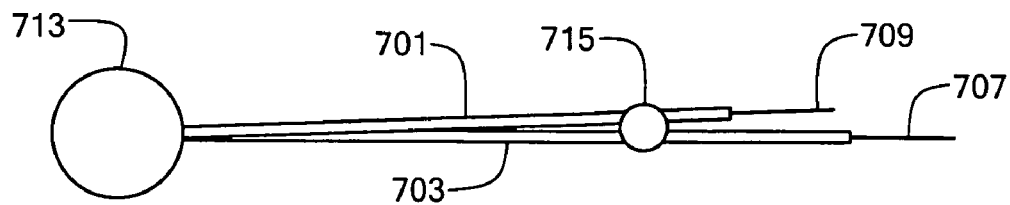
FIG. 9 is a graphical illustration of an electrode in accordance with a further embodiment of the invention.

The main electrode branch 703 and the subdivision 701 may remain substantially parallel (see FIGS. 8 and 9) through the shaft placed on the main electrode branch 703. The main electrode branch 703 and the subdivision 701 can be locked together by a clip 715 (as shown in FIG. 9) thereby preventing further displacement or disconnection of the device of the subdivision 701. In accordance with such embodiments, there is only one major electrode lead (the lead of the main electrode 703) before the subdivision point and therefore there are no electronic interferences between the main electrode lead and any lead on the subdivision 701 up to a point located at some distance from the implant housing. Manipulation of the lead of the subdivision 701 to place a device in the middle ear is easier when it is connected with the main electrode branch 703. Friction between the main electrode branch 703 and the subdivision 703 which may originate at the implant 713 is avoided. In accordance with such embodiments, less mass and value are needed for the main electrode branch 703 and the subdivision 701 than would be necessary for two separate leads each originating at the header of the implant. Attachment of the subdivision lead to the main electrode lead provides a stable system, with no flapping anywhere.

Figure 10A:
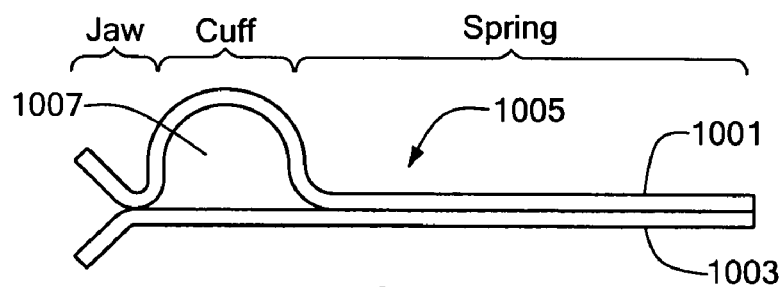
FIGS. 10A-10C are graphical illustrations of three configurations of a recording electrode for placement on the stapedius tendon or muscle.
Figure 10B:
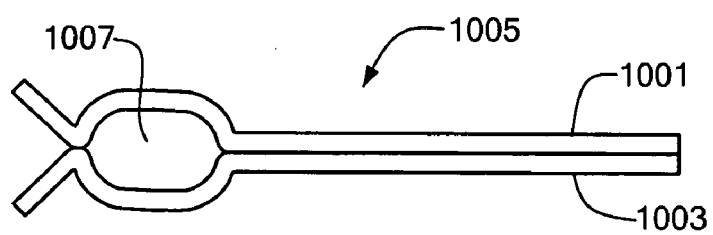
Figure 10C:
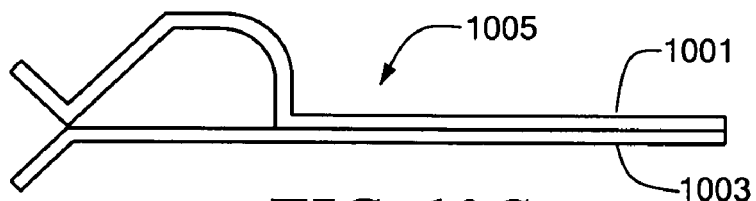
Figure 11A:
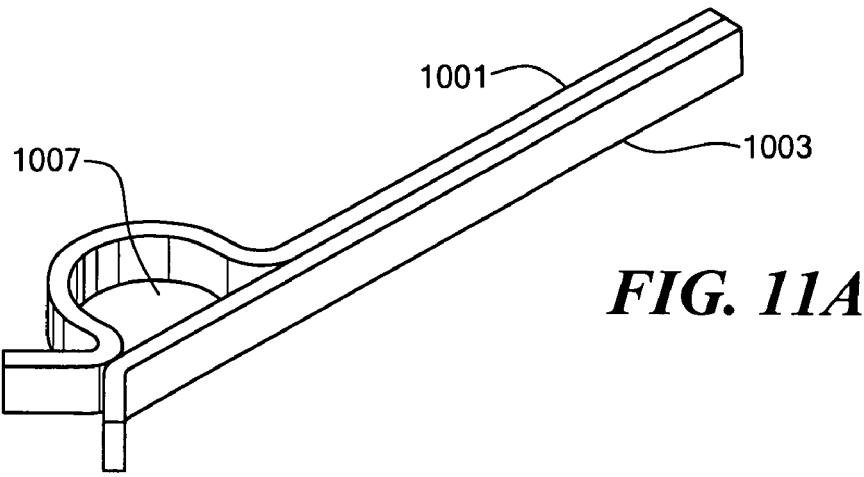
FIGS. 11A-11C are perspective views of the three configurations of FIGS. 10A-10C respectively.
Figure 11B:
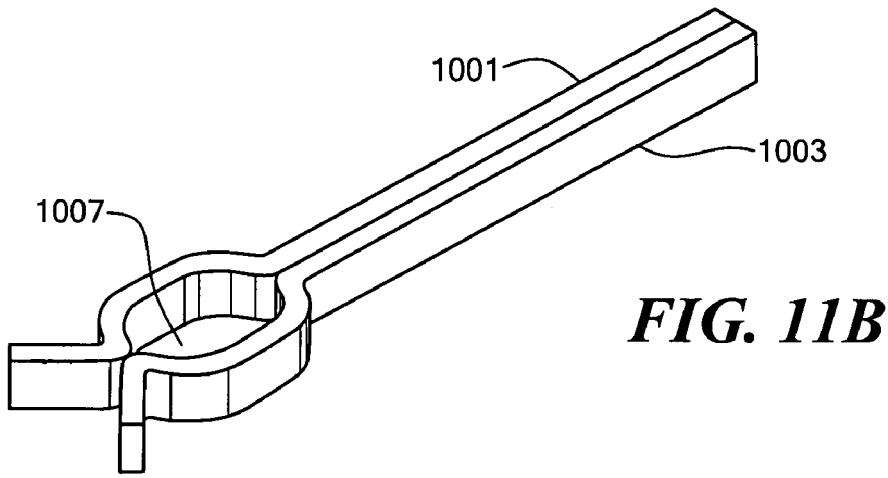
Figure 11C:
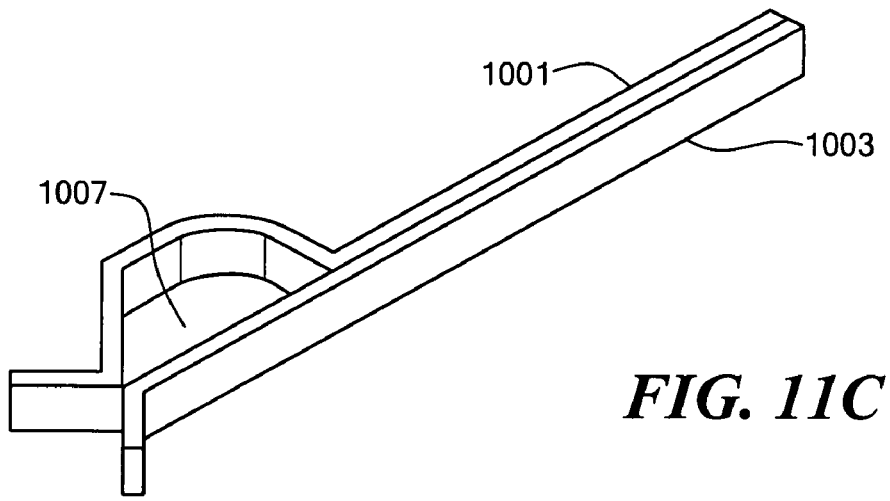

FIGS. 10A-10C are graphical illustrations of three configurations of a recording electrode for placement on the stapedius tendon and FIGS. 11A-11C are perspective views of the three configurations of FIGS. 10A-10C respectively. Each recording electrode is constructed with two branches 1001 and 1003 joined at a back end 1005 of the respective electrode. The branches 1001 and 1003 may be made of biocompatible material (e.g., platinum, iridium, Nitinol, FEP). At least one branch is made from electrically conductive material or has a conductive surface on the inside of a cuff 1007. At least one branch may be a ribbon having a preferred bending direction. The two branches 1001 and 1003 are relatively flexible and act as a spring. As an alternative, one branch may be rigid and the second branch may be highly flexible. In such a case, only the highly flexible branch makes up the spring. Electrical connection of the recording electrode to the implant circuitry through the subdivision on the main stimulating electrode branch is provided by a light flexible lead.

Figure 12A:
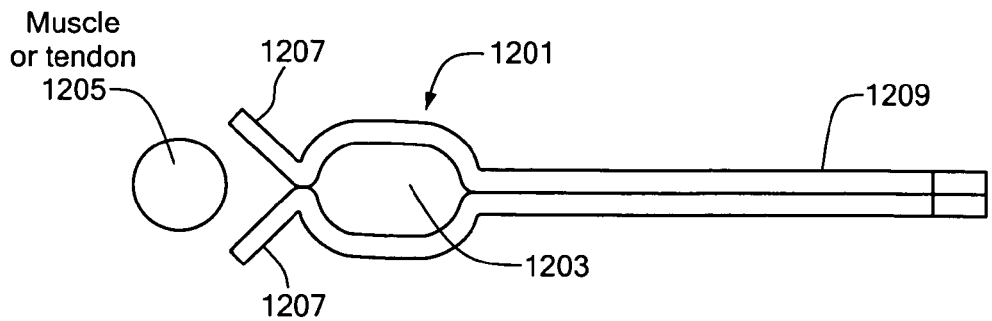
FIGS. 12A-12C are graphical illustrations of a recording electrode at various stages of deployment in a desired middle ear location.
Figure 12B:
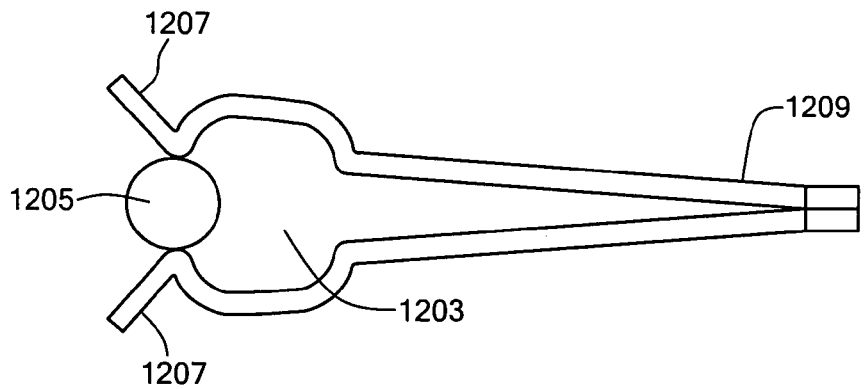
Figure 12C:
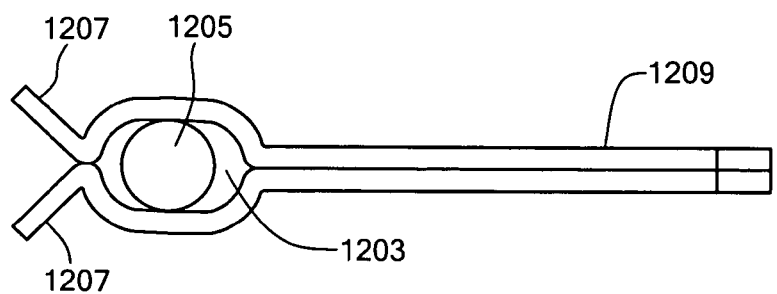

FIGS. 12A-12C are graphical illustrations of a recording electrode at various stages of deployment in a desired middle ear location. Here, a recording electrode is placed on the stapedius tendon or muscle. In order to record the stapedius muscle myogenic signal in response to electrical stimulation of sensory auditory nerve fibers, the recording electrode 1201 may be shaped as a cuff 1203 that fits around the muscle or tendon 1205. Such a cuff 1203 should be small enough to provide adequate physical contact between the metal of the recording electrode 1201 and the stapedius muscle or tendon 1205. The cuff 1203 may have a V-shaped jaws 1207 on a front end that opens up the cuff 1203 (see FIG. 12B) when being pushed against the muscle or tendon 1205 with the positioning rod. In a back end off the cuff, the recording electrode lead has an extension 1209 that serves as a spring. This extension 1209 serves to keep the cuff 1203 closed (as shown in FIG. 12C) at all times.

As shown in FIGS. 12A-12C, pushing the jaws 1207 into the muscle or tendon 1205 opens up the cuff 1203. This allows the tendon or muscle 1205 to slide into the cuff 1203 as the recording electrode 1201 is pushed further forward. The spring property of the recording electrode extension 1209 closes the cuff 1203 around the muscle or tendon 1205 once the tissue is cuffed by the recording electrode 1201. The recording electrode 1201 may be attached at the back end to a rod (not shown). The rod allows the recording electrode 1201 to be positioned at the muscle or tendon 1205 from outside the mastoidectomy and pushed onto the muscle or tendon 1205 with substantial control and without the use of cumbersome surgical tools.

The recording electrode 1201 described above does not require a tool for securing adequate physical contact between the cuff 1203 and the muscle or tendon 1205 (i.e. to close the cuff), since the recording electrode 1201 is simply pushed into the muscle or tendon 1205, and automatically opens and subsequently closes. The recording electrode 1201 may be loaded on the tendon or muscle 1205 without having to be wrapped from behind the tendon or muscle 1205, and extra drilling is not required to load the muscle or tendon 1205 since it is loaded from the front of the tendon or muscle 1205. Additionally, loading of the tendon or muscle 1205 may take place with a direct line of sight. The recording electrode 1201 may be designed to fit various muscle or tendon sizes, and removal of the recording electrode 1201 from the muscle or tendon 1205 is possible by simple pulling back on the springy electrode. The design of the recording electrode 1201 permits variation of size, ease of attachment (via the angle of V-shaped jaws and the closing force of spring), and ease of removal (via the closing force of spring and the shape of cuff).

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. An electrode for use with a cochlear implant capable of being implanted in a subject, the electrode comprising:
    a main electrode branch having an electrode array with at least one stimulating electrode and having a cochleostomy site located anterior to the electrode array;
    an adjustable subdivision having an attachment end and a tip, the adjustable subdivision connected to the main electrode branch at the attachment end anterior to the cochleostomy site and having a device located toward the tip, the device providing functions to a middle ear of the subject; and
    a shaft located on the main electrode branch anterior to the cochleostomy site, the shaft allowing the device to be adjusted relative to the main electrode branch.

2. An electrode according to claim 1, wherein the adjustable subdivision is attached to a rod like manipulator near the tip.

3. An electrode according to claim 2, wherein the rod like manipulator is movable through the shaft located on the main electrode branch.

4. An electrode according to claim 1, wherein the adjustable subdivision is movable through the shaft located on the main electrode branch.

5. An electrode according to claim 1,
    wherein the subdivision may be affixed to any part of the main electrode branch anterior to the cochleostomy site.

6. An electrode according to claim 1,
    wherein the adjustable subdivision includes a transducer.

7. An electrode according to claim 1,
    wherein the adjustable subdivision provides a recording electrode to record signals from the middle ear.

8. An electrode according to claim 7, wherein the recording electrode comprises:
    a first section, the first section including a front end and being configured such that it may be disposed about a stapedius muscle of the subject's middle ear; and
    a second section, the second section including a back end, the back end including a flexible extension for positioning the first section around the stapedius muscle.

9. An electrode according to claim 8, wherein the front end includes jaws that open to allow positioning of the first section about the stapedius muscle and wherein the flexible extension closes the jaws about the stapedius muscle.

10. An electrode according to claim 8, further including a rod for positioning the first section about the stapedius muscle from outside a mastoidectomy.

11. An electrode according to claim 8, further comprising a rod for positioning the first section about the stapedius muscle from anterior to a cochleostomy site.

12. An electrode according to claim 8, wherein the first section includes a transducer.

13. An electrode according to claim 8, wherein the first section is shaped as a cuff.

14. An electrode according to claim 1,
    wherein the adjustable subdivision provides a measuring electrode to sense a bio potential in the middle ear.

15. An electrode according to claim 1,
    wherein the adjustable subdivision provides a ground current electrode in the middle ear.

16. An electrode according to claim 1,
wherein the adjustable subdivision provides a reference electrode in the middle ear.

17. An electrode according to claim 1,
wherein the adjustable subdivision provides an implantable hearing aid in the middle ear.

18. An electrode according to claim 1,
wherein the adjustable subdivision provides an implantable microphone in the middle ear.

19. An electrode according to claim 1,
wherein the adjustable subdivision provides a biocompatible transducer in the middle ear.

20. An electrode according to claim 1,
wherein the adjustable subdivision provides a drug delivery device in the middle ear.

* * * * *